United States Patent [19]

Grambow et al.

[11] Patent Number: 5,041,662

[45] Date of Patent: Aug. 20, 1991

[54] PROCESS FOR THE PRODUCTION OF GUANIDINE NITRATE FROM UREA AND AMMONIUM NITRATE

[75] Inventors: Clemens Grambow, Seebruck; Wolfgang Kristof, Trostberg; Peter Reitsamer, Waldkraiburg; Kurt Scheinost, Trostberg, all of Fed. Rep. of Germany

[73] Assignee: SKW Trostberg Aktiengesellschaft, Trostberg, Fed. Rep. of Germany

[21] Appl. No.: 488,497

[22] Filed: Mar. 2, 1990

[30] Foreign Application Priority Data

Dec. 29, 1987 [DE] Fed. Rep. of Germany ....... 3744358

[51] Int. Cl.$^5$ ............................................. C07C 277/08
[52] U.S. Cl. .................................................... 564/242
[58] Field of Search ........................................ 564/242

[56] References Cited

U.S. PATENT DOCUMENTS

| | | | |
|---|---|---|---|
| 2,949,484 | 8/1960 | Mackay | 564/242 |
| 3,043,878 | 7/1962 | Roberts et al. | 564/242 |
| 4,390,726 | 6/1983 | Thoma | 564/242 |
| 4,535,185 | 8/1985 | Thoma | 564/242 |

FOREIGN PATENT DOCUMENTS 527747  7/1956  Canada ............................... 564/242

Primary Examiner—James H. Reamer
Attorney, Agent, or Firm—Felfe & Lynch

[57] ABSTRACT

The present invention provides a process for the production of guanidine nitrate by the reaction of urea and excess ammonium nitrate in the presence of a silicon dioxide catalyst at an elevated temperature, wherein the molten reaction mixture containing the dispersed catalyst is passed in a cycle, a branch current of the reaction mixture is continuously separated off by filtration in such a manner that the catalyst remains in circulation and consumed urea and ammonium nitrate are supplemented corresponding to the removal of the product.

11 Claims, 1 Drawing Sheet

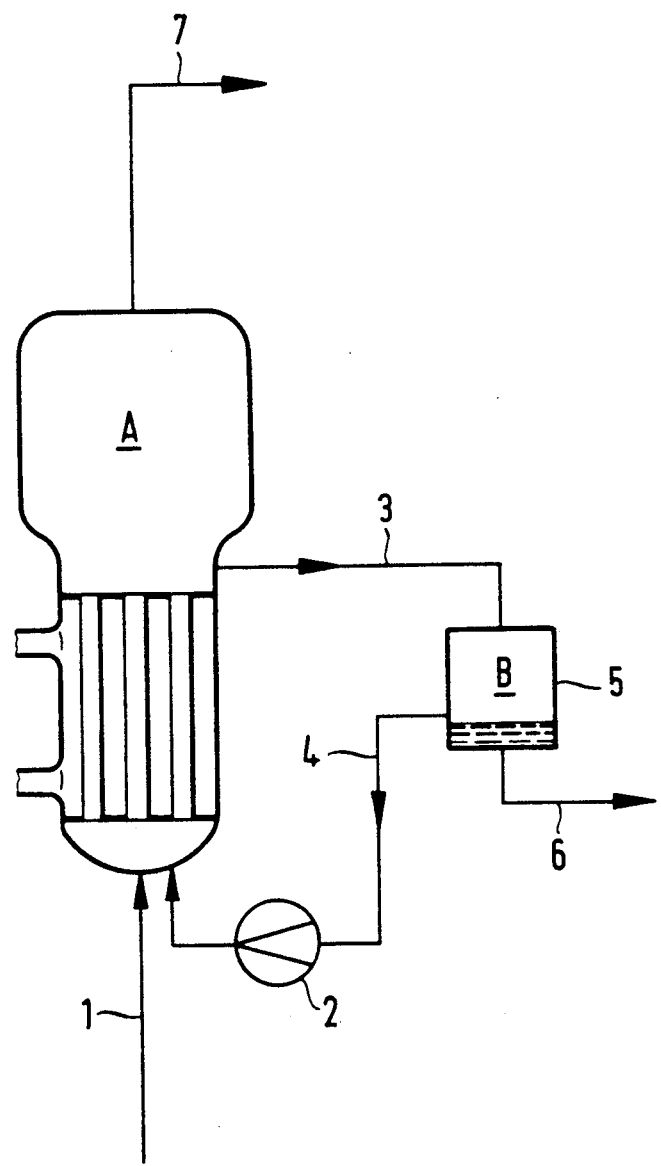

PROCESS FOR THE PRODUCTION OF GUANIDINE NITRATE FROM UREA AND AMMONIUM NITRATE

This application is a continuation of application Ser. No. 284,258, filed Dec. 14, 1988, now abandoned.

The present invention is concerned with a process for the production of guanidine nitrate from urea and excess ammonium nitrate at an elevated temperature in the presence of a silicon dioxide catalyst.

Such a process is known from Federal Republic of Germany Patent Specification No. 31 11 619 in which the catalyst must be regenerated after only a short period of time because this is inactivated by the organic by-products (triazine derivatives) formed in the course of the reaction. For this purpose, the catalyst must be filtered off from the reaction melt and dehydrated under certain pressure and temperature conditions or again reactivated subsequently by heating.

An improvement of this expensive and laborious working up is made possible by the process according to Federal Republic of Germany Patent Specification No. 32 36 221. After the reaction has taken place, the catalyst is thereby separated off from the reaction melt by filtration and slurried several times at 135° to 200° C. with the components of the reaction mixture and by-products adhering thereto using molten ammonium nitrate or an ammonium nitrate/urea mixture and again filtered off.

This method is also relatively expensive, especially the purification of the catalyst, so that a continuous process on a technical scale is not possible. Furthermore, in the case of this process, too, the catalyst has only a limited shelf-life.

Therefore, it is an object of the present invention to provide a process for the production of guanidine nitrate from urea and excess ammonium nitrate in the presence of a silicon dioxide catalyst at an elevated temperature which does not suffer from the disadvantages of the prior art but, on the contrary, makes possible, in a technically simple manner, a working up of the reaction products and of the catalyst which is as optimal as possible and which also permits a continuous process on a technical scale.

Thus, according to the present invention, there is provided a process for the production of guanidine nitrate by the reaction of urea and excess ammonium nitrate in the presence of a silicon dioxide catalyst at an elevated temperature, wherein molten reaction mixture containing the dispersed catalyst is passed in a cycle, a branch current of the reaction mixture is continuously separated off by filtration in such a manner that the catalyst remains in circulation and consumed urea and ammonium nitrate are supplemented corresponding to the removal of product.

Surprisingly, we have found that, in this way, the laborious separate filtration of the hot reaction melt, as well as the rinsing with an ammonium nitrate or ammonium nitrate-urea melt according to Federal Republic of Germany Patent Specification No. 32 36 221 can be omitted and that the shelf-life of the catalyst can be considerably prolonged.

In the case of the process according to the present invention, the reaction mixture consisting of urea, ammonium nitrate and silicon dioxide catalyst is reacted at the usual temperature at 175° to 225° C. and especially at 180° to 200° C. The weight ratio of urea to ammonium nitrate is from 1:1 to 1:6 and preferably from 1:2 to 1:3. The silicon dioxide catalyst is used in an amount of from 10 to 20% by weight, referred to the weight of the mixture used consisting of urea and ammonium nitrate.

The reaction to guanidine nitrate can be carried out in conventional reactors in which the necessary heat of reaction can be introduced from the outside. In practice, recycle reactors and tube bundle reactors have proved to be particularly useful.

An important feature of the present invention is the circulation of the reaction melt, which can be carried out with technically conventional devices, for example pumps and the like.

In this way, provision is made, in particular, for a good heat supply and for a high turbulence, as well as an intensive intermixing of the reaction components with the catalyst, which are advantageous for a rapid reaction and a high throughput. After reaction has taken place, a branch current of the reaction product, which consists of guanidine nitrate, the excess and unreacted ammonium nitrate, as well as some urea, is continuously branched off and filtered off from the catalyst. The catalyst thus remains in the reaction part and is passed continuously in circulation with the reaction mixture. With the branch current of molten reaction product, which is filtered off from the catalyst, apart from the reaction mixture, small amounts of impurities are also removed from the reaction circulation which would otherwise coat the catalyst and inactivate it after a short period of time. By means of the continuous removal of these impurities, it is ensured that the concentration of harmful materials in the reaction part is always kept so low that practically no inactivation of the catalyst can occur even after long periods of use. The sole losses of catalyst occur due to mechanical abrasion, very finely dispersed catalyst particles thereby resulting which also cannot be retained by conventional filters but rather leave the reaction circulation with the product branch current and only become noticeable after a certain period of time. If these losses resulting from mechanical abrasion are compensated gradually, the life of the catalyst in the process according to the present invention is practically unlimited.

The separation of the product branch current from the catalyst by filtration can be carried out with the technically conventional filtration devices. There can be used filter plates with appropriate temperature-resistant filter materials, for example glass fibres, sintered metals or textile fabrics. Because of their relatively small filter area, however, only limited throughputs are possible with these filtration devices. For higher throughput capacities, it is recommended to use filter candles.

In order to achieve a clean separation of the product stream from the catalyst, which usually has a particle size of $90\% < 20\mu$, the filter should have a clearance threshold of $<5\mu$ and preferably of 2 to $3\mu$.

The filtration or separation of the product stream from the catalyst can take place at practically any point of the circulation insofar as this is technically possible and suitable.

In a preferred embodiment of the present invention, the filtration device can be arranged within the reactor, for example in the form of a bottom plate, and the product stream drawn off at the lower part of the reactor, whereas the reaction mixture is passed in an otherwise closed circulation.

According to a further variant of the process, the filtration device is arranged outside of the reactor in the reaction circulation. This will, in particular, be the case when high throughputs are required and the filtration device must be made correspondingly large, for example in the form of a filter candle device.

The filtration devices used must be maintained at a temperature above the melting temperature of the reaction product, which is about 140° C., in order to prevent a blocking of the filter by product crystallising out. This blocking can be prevented by the arrangement of a stirring device in the neighbourhood of the filter. The reaction product freed from catalyst, consisting essentially of guanidine nitrate, as well as urea and ammonium nitrate, can be worked up according to known methods (cf. for example Federal Republic of Germany Patent Specification No. 31 11 619). The melt is usually dissolved in water, the guanidine nitrate is crystallised out and filtered off, the preponderantly ammonium nitrate containing mother liquor is evaporated if necessary and the residue again recycled to the reactor. However, the recycling into the reactor is only advantageous when the organic impurities in the form of triazine derivatives have previously been separated off at some stage of the working up, in order to prevent an enrichment in the reactor of these compounds, which, as previously mentioned, inactivate the catalyst. The separation of these organic impurities is known, for example, from Federal Republic of Germany Patent Specification No. 31 11 619.

In order to maintain the continuous carrying out of the reaction, the starting compounds urea and ammonium nitrate are introduced in the necessary weight ratio into the reactor in an amount which is equivalent to the removed branch current of molten reaction product, so that the reaction circuit shows a constant weight balance. It must thereby be taken into account that a stoichiometric proportion of the urea and ammonium nitrate also reacts to give ammonium carbamate which separates out from the liquid melt in gaseous form. The replenishing of the starting compounds can take place batchwise or continuously.

The process according to the present invention is explained in more detail in a preferred embodiment, with reference to the accompanying drawing:

The starting compounds urea and ammonium nitrate are introduced via a pipe (1) into a heated tube bundle reactor A, in which there is already present the necessary amount of catalyst, in the desired weight ratio. The reaction mixture is pumped by a pump (2) via pipe (3) into a filtration device (B) and via pipe (4) back again into the reactor A. By means of a filter (5), a part of the liquid product stream is separated from the catalyst and passed via a pipe (6) to further working up. The ammonium carbamate also formed by the reaction is withdrawn via a pipe (7) at the head of the reactor.

The process according to the present invention, which provides a qualitatively valuable guanidine nitrate, is, because of the small technical expense and of the extremely long life of the catalyst, outstandingly suitable for technical use.

The following Example is given for the purpose of illustrating the present invention:

EXAMPLE

In a tube bundle reactor according to the FIGURE of the accompanying drawing are placed 84 kg. of ammonium nitrate, 40 kg. of urea and 18 kg of silica gel catalyst and heated to 180° to 200° C. The reaction mixture is passed by a pump in a circuit according to the FIGURE, in which a filtration device is arranged. Into the filtration device is incorporated a filter bottom, consisting of a coarse supporting fabric with a fine filter laid thereupon (two-layered glass fibre layer of Type 94 810 of the firm Gradl). Beginning after 2 hours, a liquid product stream, consisting of 25 g./hour ammonium nitrate, 1.5 kg./hour urea, as well as 15.5 kg./hour guanidine nitrate, is withdrawn continuously via the filter bottom and passed on for further working up. At the same time, the reactor is continuously supplied with a fresh starting mixture consisting of 36 kg./hour of ammonium nitrate and 16.5 kg./hour of urea. At the head of the reactor, 10.5 kg. of ammonium carbamate are drawn off per hour. The catalyst remaining in the reactor has a life of more than 1000 hours.

We claim:

1. The process for the production of guanidine nitrate by the reaction of urea and ammonium nitrate in a weight ratio of 1:1 to 1:6 in the presence of a silicon dioxide catalyst at a temperature of 175 to 225° C., wherein the molten reaction mixture containing the dispersed catalyst is continuously cycled through the reaction vessel, a branch current of the reaction mixture is continuously separated by filtration in such a manner that the catalyst remains in circulation, and consumed urea and ammonium nitrate are supplemented corresponding to the rate of removal of the reaction product.

2. The process according to claim 1, wherein the reaction temperature is 180° to 200° C.

3. The process according to claim 1, wherein the weight ratio of urea to ammonium nitrate is from 1:2 to 1:3.

4. The process according to claim 1, wherein the silicon dioxide catalyst is used in an amount of from 10 to 20% by weight, referred to the weight of the mixture of urea and ammonium nitrate.

5. The process according to claim 1, wherein the filtration is carried out with the aid of a filter plate.

6. The process according to claim 1, wherein filter candles are used for the filtration.

7. The process according to claim 1, wherein a filter with a clearance threshold of $<5\mu$ is used.

8. The process according to claim 7, wherein a filter with a clearance threshold of from 2 to $3\mu$ is used.

9. The process according to claim 1, wherein the filtration device is arranged within the reactor.

10. The process according to claim 1 wherein the filtration device is arranged outside of the reactor in the reaction mixture circulation.

11. The process according to claim 1, wherein the product stream is worked up after the filtration, and the unreacted starting compounds ammonium nitrate and urea thereby obtained are returned to the reaction mixture circulation.

* * * * *

UNITED STATES PATENT AND TRADEMARK OFFICE
CERTIFICATE OF CORRECTION

PATENT NO. : 5,041,662

DATED : August 20, 1991

INVENTOR(S) : Clemens Grambow et al

It is certified that error appears in the above-identified patent and that said Letters Patent is hereby corrected as shown below:

Cover page, after item [22], insert --Related U.S. Application Data [63] Continuation of Ser. No. 284,258, December 14, 1988, abandoned--.

Signed and Sealed this

Sixteenth Day of March, 1993

Attest:

STEPHEN G. KUNIN

Attesting Officer

Acting Commissioner of Patents and Trademarks